(12) United States Patent
Hansen et al.

(10) Patent No.: US 7,175,055 B2
(45) Date of Patent: Feb. 13, 2007

(54) FRONTLOADED INJECTION DEVICE

(75) Inventors: Michael Ejstrup Hansen, Veflinge (DK); Claus Schmidt Moller, Fredensborg (DK); Christian Peter Enggaard, Hillerod (DK); Andre Larsen, Dragor (DK)

(73) Assignee: Novo Nordisk, A/S, Bagsvaerd (DK)

( * ) Notice: Subject to any disclaimer, the term of this patent is extended or adjusted under 35 U.S.C. 154(b) by 0 days.

(21) Appl. No.: 10/646,295

(22) Filed: Aug. 22, 2003

(65) Prior Publication Data
US 2004/0108339 A1 Jun. 10, 2004

Related U.S. Application Data

(60) Provisional application No. 60/416,858, filed on Oct. 8, 2002.

(30) Foreign Application Priority Data

Aug. 29, 2002 (DK) ............... 2002 01269

(51) Int. Cl.
*B65D 88/54* (2006.01)
(52) U.S. Cl. ............ 222/326; 222/325; 222/327; 222/386; 604/207; 604/211; 604/232; 604/235
(58) Field of Classification Search ........ 222/325–328, 222/80–81, 386; 604/232–235, 211, 207
See application file for complete search history.

(56) References Cited

U.S. PATENT DOCUMENTS

| | | | | |
|---|---|---|---|---|
| 2,392,196 A | 1/1946 | Smith | ............ | 128/218 |
| 2,956,563 A | * 10/1960 | Sarnoff | ............ | 604/232 |
| 3,115,135 A | 12/1963 | Sarnoff | | |
| 3,144,178 A | 8/1964 | Sarnoff et al. | | |
| 3,556,099 A | * 1/1971 | Knight et al. | ............ | 604/232 |
| 3,880,162 A | * 4/1975 | Simmons | ............ | 604/197 |
| 4,314,556 A | * 2/1982 | Ma | ............ | 604/187 |
| 4,973,318 A | * 11/1990 | Holm et al. | ............ | 604/208 |
| 5,000,744 A | 3/1991 | Hoffman et al. | ............ | 604/232 |
| 5,002,537 A | * 3/1991 | Hoffman et al. | ............ | 604/232 |
| 5,078,698 A | 1/1992 | Stiehl et al. | ............ | 604/235 |
| 5,244,465 A | 9/1993 | Michel | ............ | 604/208 |
| 5,496,286 A | 3/1996 | Stiehl et al. | ............ | 604/232 |
| 6,036,675 A | * 3/2000 | Thorne et al. | ............ | 604/232 |
| 6,752,798 B2 | * 6/2004 | McWethy et al. | ............ | 604/506 |

FOREIGN PATENT DOCUMENTS

| | | |
|---|---|---|
| EP | 0 513 128 B1 | 7/1991 |
| WO | 91/10460 | 7/1991 |
| WO | 97/07841 | 3/1997 |

* cited by examiner

*Primary Examiner*—Frederick C. Nicolas
(74) *Attorney, Agent, or Firm*—Marc A. Began; Richard W. Bork; Reza Green

(57) ABSTRACT

A frontloaded injection device that includes a cartridge holder into which a replaceable cartridge containing a fluid is inserted. The cartridge holder includes a closing element such as a pair of claws which are displaceable in a radial direction. The closing element is provided at the front of the injection device and locks the cartridge by gripping at the neck part of the cartridge after the cartridge has been loaded into the cartridge holder from the front of the injection device. The closing element is preferably biased in an outwardly radial direction when the locking element is moved axially out of the cartridge holder.

3 Claims, 3 Drawing Sheets

FRONTLOADED INJECTION DEVICE

CROSS-REFERENCE TO RELATED APPLICATIONS

This application claims priority under 35 U.S.C. 119 of Danish application no. PA 2002 01269 filed Aug. 29, 2002, and U.S. provisional application No. 60/416,858 filed Oct. 8, 2002, the contents of which are fully incorporated herein by reference.

FIELD OF THE INVENTION

The invention relates to injection devices comprising a cartridge holder and a dose setting and injection part by which set doses can be apportioned from a cartridge in the cartridge holder as a piston rod is successively moved into a first end of said cartridge to press a piston closing said first end of the cartridge into the cartridge which has a second end closed by a membrane, whereby a liquid stored between the piston and the membrane can be pressed out through a hollow needle which is mounted on the device so that it pierces said membrane, access to the cartridge holder being obtained by opening a first end thereof through which the first end of the cartridge can be inserted with its piston facing the piston rod which extends into the cartridge holder from a second end thereof.

By most known injection devices using changeable cartridges the cartridge holder may be unscrewed from the device to obtain access to the cartridge holder. This will make the user stand with two parts: A cartridge holder with an empty cartridge; and a dose setting and injection part with a protruding piston rod. The cartridge in the cartridge holder is then changed and the cartridge holder can be remounted on the dose setting and injection part. However, first the extending piston rod must be pushed or screwed back into the dose setting and injection part. This returning of the projecting piston rod can cause some problems as an attempt to screw back a piston rod, which is designed to be pushed back, and visa versa, may damage the piston rod or components in the dose setting and injection system. Consequently an injection device in which the piston rod cannot be reached by the user is preferred.

In a so-called front loaded device as the one described in the opening of this application the piston rod remains hidden by the cartridge holder when the front end of this holder is opened to change the cartridge. When a new cartridge is passed into the cartridge holder the piston of this cartridge abuts the piston rod and press it backward into the device when the cartridge is pressed into the cartridge holder from the open first end of this cartridge holder. The open first end of the cartridge holder may the be closed by a screw plug as it is described in EP 513 128.

As loose parts as screw plug offers possibility for skew mounting or loss of this part it is an objective of the invention to provide a closing mechanism which is integrated in the device.

SUMMARY OF THE INVENTION

This is obtained by a device as described in the opening of this application, which device is characterised in that at least one closing element is provided at the first end of the cartridge holder which closing element in its closed position forms a support for the second end of a cartridge to bar for an axial movement of the cartridge out of the cartridge holder and which closing element is displaceable in a radial direction relative to the cartridge holder so that said closing element can be moved to a position allowing a cartridge to pass axially into or out of the cartridge holder.

The cartridge holder may be provided with at least one axial element which has at its end at the second end of the cartridge holder an inward protrusion perpendicular to said axial element, which protrusions form the closure of the cartridge holder and may be moved in a radial direction relative to the cartridge holder by deflecting the end of the element carrying said inward protrusion away from its axial position and the cartridge holder In an embodiment a closure at the second end of the cartridge holder may be formed by a number of axial elements arranged to form a cylinder accommodating a each axial element having an inward protrusion perpendicular to said axial element.

The said axial elements may be biased to be deflected outwardly and may be held in an axial position by an encompassing cartridge holder having an inner diameter corresponding to the outer diameter of the arrangement of the axial elements when these are in their axial position.

A longitudinal displacement of the cartridge holder may be obtained by a closing mechanism comprising a ring which is mounted on the device and can be rotated between to rotational positions, the ring having pins extending through slots in the cartridge holder and into tracks a tubular element on which the longitudinal elements are arraged, the tracks being helically designed so that the tubular element is displaced in an axial direction when the ring is rotated from one rotational position to the other.

In another embodiment of the invention at least one closing element is mounted at a front end of the cartridge holder axially displaceable relative to said cartridge holder.

A connection may be established between the locking device and the dose setting part of the device to set the piston free to be moved backward when the closure of the cartridge holder is opened and to lock it to the dose setting part to be governed by this part when the closure is closed.

BRIEF DESCRIPTION OF THE DRAWINGS

In the following the invention is further described with references to the drawing, wherein.

DETAILED DESCRIPTION

Figure 1:
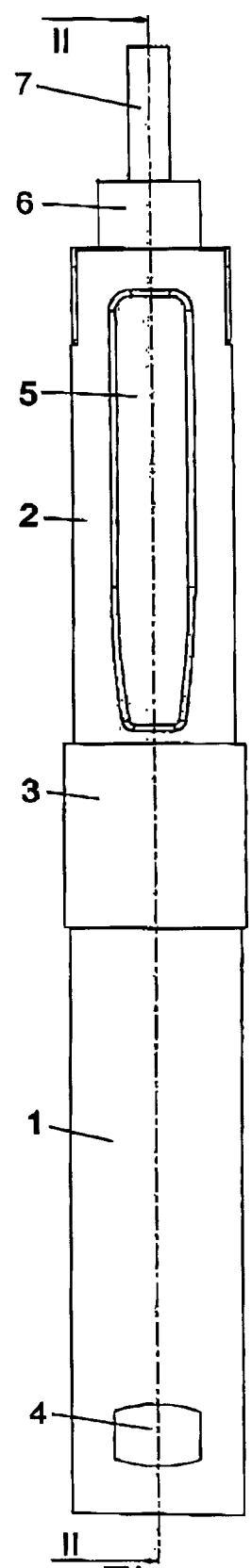
FIG. 1 shows schematically a side view of a front loadable syringe according to the invention.

FIG. 1 schematically shows a syringe according to the invention which syringe comprises a housing 1 for a dose setting and injection part, a cartridge holder 2 mounted on the housing 1, and an operation ring 3 surrounding the housing at the transition between the housing 1 and the cartridge holder 2. The housing 1 has a window 4 wherein a set dose is shown, but details of the dose setting and injection system are not shown. The cartridge holder 2 has a window 5 through which a cartridge in the cartridge holder can be visually inspected. The cartridge may be provided with a plastic top 6 onto which a not shown needle hub with an injection needle can be mounted. The possible provision of a needle is hinted by a needle cap 7.

Figure 2:
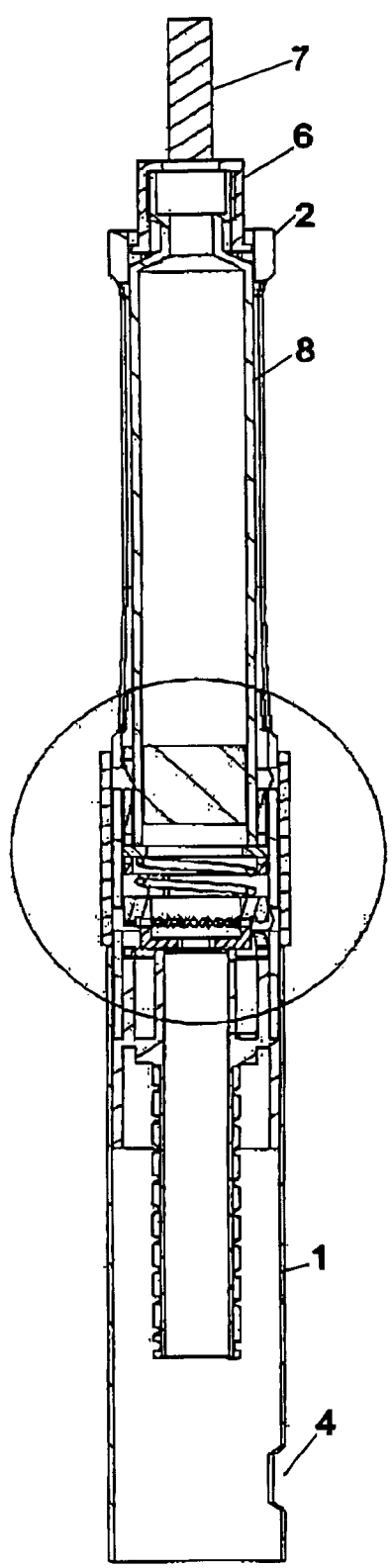
FIG. 2 shows a sectional view along the line II—II in the syringe in FIG. 1.
Figure 3:
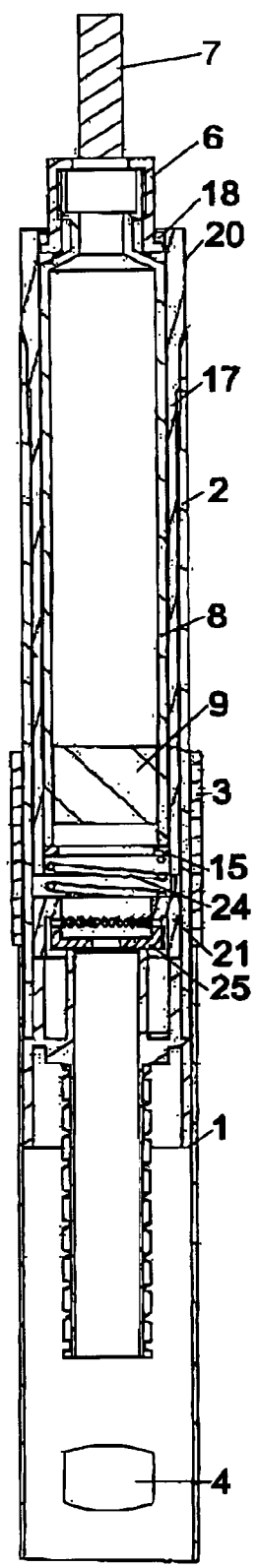
FIG. 3 shows a sectional view of the syringe in FIG. 2 rotated 90° about its axis.
Figure 4:
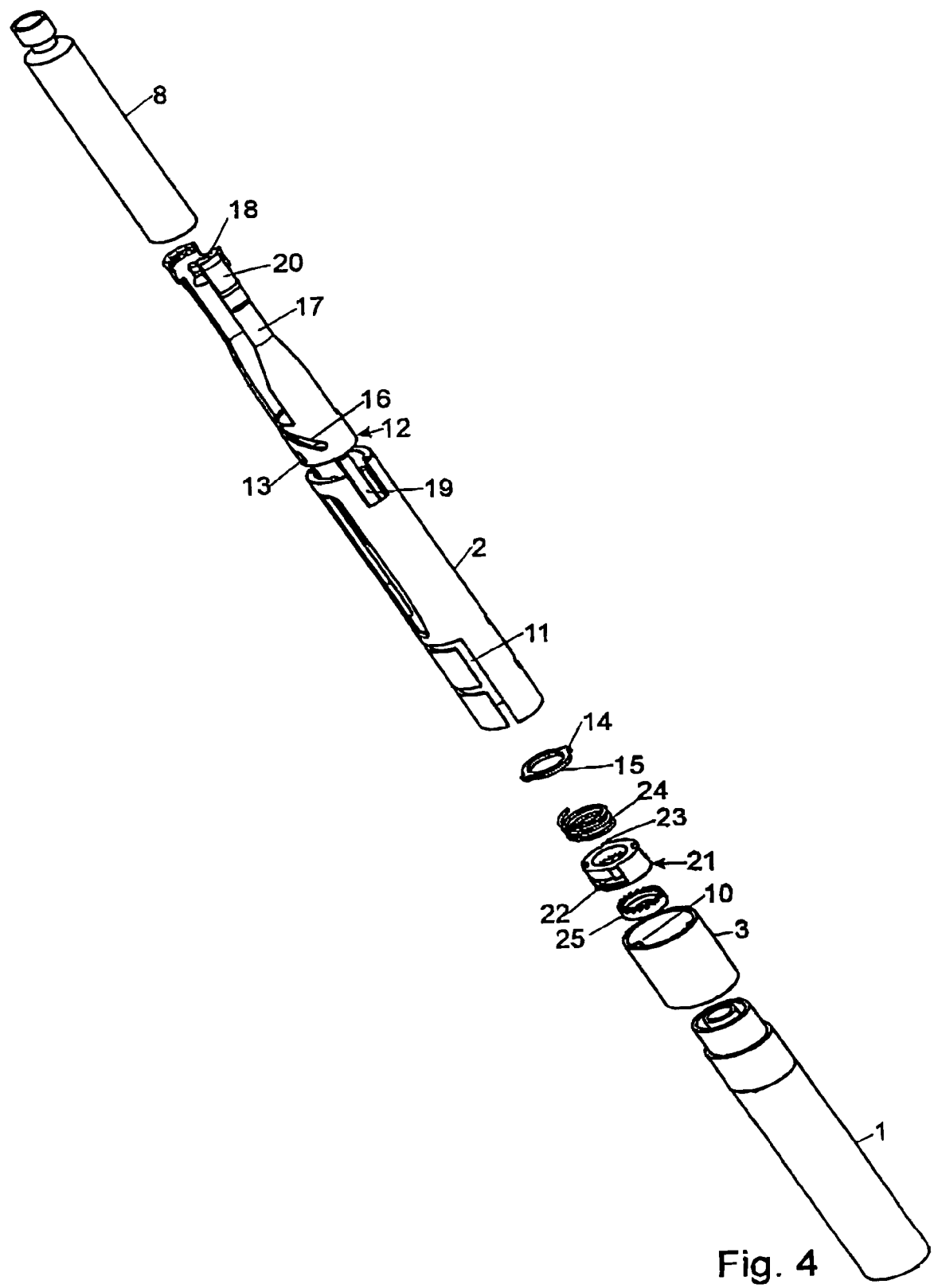
FIG. 4 shows an exploded view of the syringe in FIG. 1.
Figure 5:
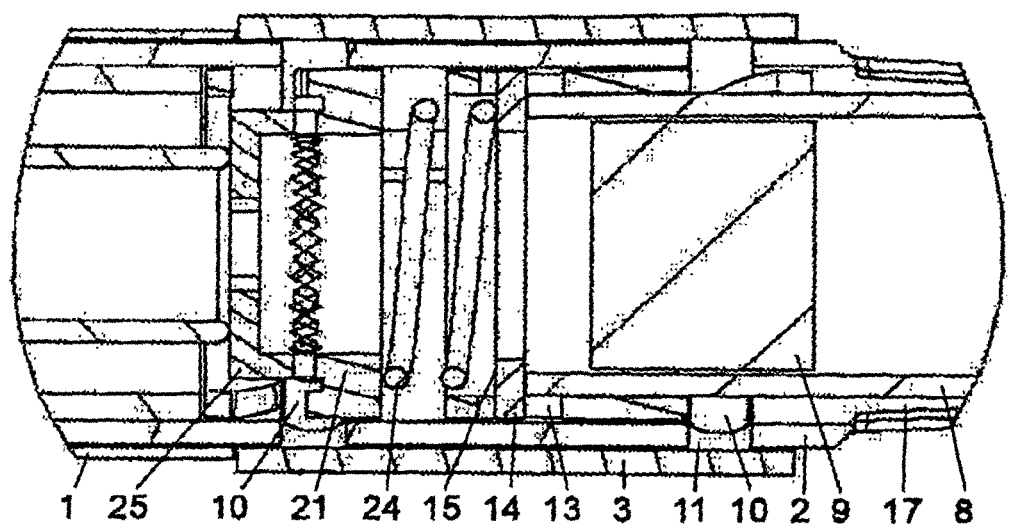
FIG. 5 shows an enlarged view of the encircled part in FIG. 2.

FIGS. 2 and 3 shows sectional views of the syringe in FIG. 1 whereas FIG. 4 shows an exploded view of this syringe. In FIG. 3 it is seen that a cartridge 8 mounted in the cartridge holder 2 has a piston 9 which can be moved into the cartridge by a not shown piston rod which is successively moved outward from the dose setting and injection system when doses are set and injected. The function of the dose setting system implies that the piston rod cannot rotate relative to the housing during dose setting and injection. When the piston rod is allowed to rotate the extending part of it can easily be pressed back into the dose setting and injection system.

As it is seen in FIG. 4, the cartridge holder 2 is a tubular element provided with windows 5 for cartridge inspection and having at its end adjacent to the housing 1 of the dose setting and injection system a F-shaped cut out 11 which allows mounting of an operation ring 3 which has on its inner wall pins 10 with an axial distance corresponding to the distance between the horizontal parts of the F-shaped cut out. The mounting is obtained by passing the pins 10 along the vertical part of the F-shaped cut out 11. In FIG. 4 only one F-shaped cut out is seen but a similar cut out is provided rotationally displaced 180° from the shown cut out.

A clamping member 12 has a tubular bottom part which has diametrically opposed axial cut outs 13 in which correspondingly diametrically opposed protrusions 14 at the perimeter of a ring 15 are guided to form an axially displaceable bottom in the clamping member 12. Said bottom part further has diametrically opposed cut outs 16 which are not perpendicular to the axis of the clamping member 12 but rather form apart of a helix. The bottom part further carries two diametrically opposed tongues 17 which are biased to diverge outwardly away from the axis of the clamping member 12. At their outer ends the tongues 17 are provided with closing members 18 which are moved radial inward when the tongues 17 are forced to attain an axial direction.

The clamping member 12 is mounted in the cartridge holder 2 which has at its end opposite the dose setting and injection system longitudinal cut outs 19 in which ribs 20 at outer wall of the end of the tongues 17 can be guided. The operation ring 3 is mounted so that a pair of diametrically opposed pins 10 on this ring grips through the upper vertical part of the F of the F-shaped cut out into the cut out 16 in the bottom part of the clamping member 12.

A coupling ring 21 having in its outer wall diametrically opposed recesses 22, each comprising two axially displaced parts perpendicular to the axis of the syringe connected by a part which is not perpendicular to said axis, is mounted in the cartridge holder 2 so that a set of diametrically opposed pins on the inner wall of the operation ring 3 grips through the lover vertical part of the F of the F-shaped cut outs into said recesses 22. The coupling ring 21 further has at its outer cylindrical wall splines 23 which engage axial recesses in the cartridge holder to make the coupling ring inrotatable in the cartridge holder. A spring 24 is mounted between the coupling ring 21 and the bottom ring 15 of the clamping member 12. Finally the coupling ring 21 is at its end surface turning away from the cartridge holder provided with circumferential three angled teeth which can cooperate with similar teeth on a piston rod guide ring 25 which has a not round central opening through which a correspondingly not round not shown piston rod projects from the dose setting and injection system.

When the described components has been mounted in the cartridge holder 2 this holder is by gluing or welding or any other method secured to the housing 1.

In the FIGS. 2 and 3 the syringe is ready for use with a cartridge held in the cartridge holder. The operation ring 3 is in a position wherein its pins 10 gripping through the F-shaped cut out into the recess 16 of the syringe clamping member 12 engaging the parts at the foremost ends of these recesses 16 which parts are shaped as not helical landings which runs perpendicular to the axis of the clamping member 12. Thereby the clamping member 12 is held in a retracted position in the cartridge holder in which position the closing members 18 is in their radially innermost position in which they grip over a neck part of the cartridge 8 and bar for an outward movement of said cartridge 8. At the same time the pins gripping through the lover vertical part of the F of the F-shaped cut out into the recess 22 of the coupling ring 21 keep this ring 21 in a position wherein its triangular teeth engages the teeth of the piston rod guide ring 25 through which the not shown piston rod is guided, and this way the piston rod is locked against rotation relative to the housing 1.

When in FIG. 4 the operation ring 3 is rotated to the left the, pins engaging the recess 16 of the clamping member will move this member outward in the cartridge holder. The tongues 17 which were forced to their axial position by the cartridge holder will now diverge bringing the closing members away from the cartridge and provide an opening through which the cartridge can be drawn out through the end of the cartridge holder 2. At the same time the other set of pins 10 which engages the recesses of the coupling ring 21 will against the force of the spring 24 move this ring away from the dose setting and injection system and bring its teeth out of engagement with the teeth of the piston rod guide ring 25. This will allow the piston rod guide ring 25 and the not shown piston rod to rotate so that the piston rod can by the insertion of a new cartridge be pressed back in to the dose setting and injection system. When a new cartridge has been moved into the cartridge holder, the operation ring 3 is rotated rightward whereby its pins 10 engaging the helical cut out 16 will draw the clamping member 12 into the cartridge holder and the closing members 18 will be moved radially inward in front of the cartridge to maintain it in the cartridge holder. At the same time the coupling ring 21 is by the other set of pins which engage the recesses 22 in this coupling ring moved toward the housing 1 whereby the coupling teeth of this ring is brought into engagement with the teeth on the piston rod guide ring 25. This will lock the piston rod against rotation whereby dose setting and injection is again allowed.

Figure 6:
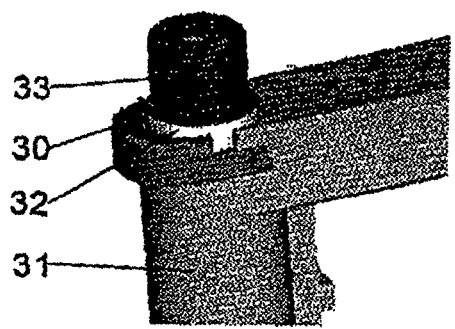
FIG. 6 shows a detail of another embodiment of a front loaded device with its closure open.
Figure 7:
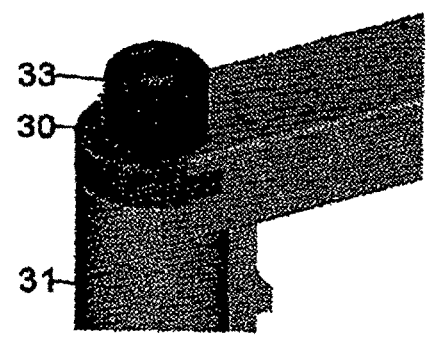
FIG. 7 shows the embodiment in FIG. 6 with its closure closed.

FIGS. 6 and 7 shows another embodiment of a front loaded injection device wherein a closing element 30 can be moved relative to a second closing element which is integral with the device. The closing element 30 is moved radially relative to a cartridge holder 31 providing an opening which allows insertion of a cartridge 32. By pressing the plastic top 33 mounted on a neck part of the cartridge, the cartridge is moved so far into the cartridge holder 31 that the closing element can be moved axially relative to the cartridge towards the second closing element so that the diameter of the opening formed by the two closing elements is smaller than the diameter of the cartridge which is in this way supported at its neck part.

We claim:

1. An injection device from which doses can be apportioned from a medicament containing cartridge wherein the injection device comprises
- a cartridge holder (2);
- an axial element (17) provided at the first end of the cartridge holder (2);
- an inward protrusion (18) perpendicular to the axial element (17), the protrusion forming the closure of the cartridge holder being moveable in a radial direction relative to the cartridge holder (2), being biased to be deflected outwardly;
- a ring (3) mounted on the device and being rotatable between a first position and a second position, the ring having pins (10) extending through slots (11) in the cartridge holder (2) and into tracks (16) in a tubular element (12) on which the axial element (17) are arranged, the tracks (16) being helical so that the tubular element (12) is displaced in an axial direction when the ring (3) is rotated from the first position to the second position and whereby the axial element (17) when moved axially out of the cartridge holder (2) is deflected outwardly.

2. The device of claim 1, further comprising a dose setting and injection mechanism.

3. the device of claim 2, wherein the dose setting mechanism comprises a window (4) in which the size of a set dose can be viewed.

* * * * *